US006984763B2

(12) United States Patent
Schweizer et al.

(10) Patent No.: US 6,984,763 B2
(45) Date of Patent: *Jan. 10, 2006

(54) OXIDATIVE HALOGENATION AND OPTIONAL DEHYDROGENATION OF C3+HYDROCARBONS

(75) Inventors: Albert E. Schweizer, Midland, MI (US); Mark E. Jones, Midland, MI (US); Daniel A. Hickman, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 73 days.

This patent is subject to a terminal disclaimer.

(21) Appl. No.: 10/478,265

(22) PCT Filed: Apr. 23, 2002

(86) PCT No.: PCT/US02/13011

§ 371 (c)(1),
(2), (4) Date: Nov. 18, 2003

(87) PCT Pub. No.: WO02/094750

PCT Pub. Date: Nov. 28, 2002

(65) Prior Publication Data

US 2004/0158110 A1    Aug. 12, 2004

Related U.S. Application Data

(60) Provisional application No. 60/293,123, filed on May 23, 2001.

(51) Int. Cl.
C07C 17/00    (2006.01)
(52) U.S. Cl. .................. 570/216; 570/224; 570/230; 570/243; 570/247; 570/248
(58) Field of Classification Search ................ 570/216, 570/224, 230, 243, 247, 248
See application file for complete search history.

(56) References Cited

U.S. PATENT DOCUMENTS

| | | | |
|---|---|---|---|
| 2,204,733 A | 6/1940 | Miller .................. 23/219 |
| 3,149,171 A | 9/1964 | Arganbright ............ 260/655 |
| 3,488,398 A | 1/1970 | Harpring et al. ........ 260/659 |
| 3,629,354 A | 12/1971 | Beard et al. .......... 260/683.3 |
| 3,634,330 A | 1/1972 | Yerres et al. ............ 252/441 |
| 3,644,561 A | 2/1972 | Beard et al. .......... 260/683.3 |
| 3,657,367 A | 4/1972 | Blake et al. .......... 260/659 A |
| 3,658,933 A | 4/1972 | Beard et al. .......... 260/683.3 |
| 3,658,934 A | 4/1972 | Beard et al. .......... 260/683.3 |
| 3,702,311 A | 11/1972 | Beard et al. ............ 252/441 |
| 3,769,362 A | 10/1973 | Beard et al. ........ 260/677 XA |
| 3,927,131 A | 12/1975 | Ward .................. 260/654 D |
| 3,968,178 A | 7/1976 | Obrecht et al. .......... 260/658 |
| 3,968,200 A | 7/1976 | Tsao ................... 423/488 |
| 4,025,461 A | 5/1977 | Croce et al. ............ 252/462 |
| 4,042,640 A | 8/1977 | Tsao .................... 260/659 |
| 4,046,821 A | 9/1977 | Croce et al. .......... 260/654 A |
| 4,046,823 A | 9/1977 | Gordon et al. ........ 260/662 R |
| 4,100,211 A | 7/1978 | Magistro .............. 260/656 R |
| 4,110,251 A | 8/1978 | Lauder et al. ............ 252/442 |
| 4,230,668 A | 10/1980 | Sheely et al. ............ 422/140 |
| 4,300,005 A | 11/1981 | Li ........................ 570/224 |
| 4,319,062 A | 3/1982 | Boozalis et al. ......... 570/220 |
| 4,323,482 A | 4/1982 | Stiles et al. ............ 252/462 |
| 4,329,525 A | 5/1982 | Riegel et al. ........... 570/191 |
| 4,375,569 A | 3/1983 | Kroenke et al. ......... 570/224 |
| 4,402,942 A | 9/1983 | Melin .................... 424/177 |
| 4,405,500 A | 9/1983 | Muller et al. ........... 252/433 |
| 4,460,699 A | 7/1984 | Convers et al. ........... 502/84 |
| 4,462,970 A | 7/1984 | Pastor et al. ............ 423/263 |
| 4,523,040 A | 6/1985 | Olah ..................... 568/671 |
| 4,528,174 A | 7/1985 | Schmidhammer et al. .. 423/488 |
| 4,529,410 A | 7/1985 | Khaladji et al. ........... 51/309 |
| 4,590,216 A | 5/1986 | Dombek .................. 518/700 |
| 4,727,201 A | 2/1988 | Cobb .................... 570/202 |
| 4,737,594 A | 4/1988 | Olah .................... 570/222 |
| 4,754,088 A | 6/1988 | Schmidhammer et al. .. 570/247 |
| 4,766,103 A | 8/1988 | Cobb .................... 502/217 |
| 4,769,504 A | 9/1988 | Noceti et al. ........... 585/415 |
| 4,783,564 A | 11/1988 | Piotrowski et al. ....... 570/254 |
| 4,849,562 A | 7/1989 | Buhs et al. ............. 570/241 |

(Continued)

FOREIGN PATENT DOCUMENTS

DE    237 058 A3    7/1986

(Continued)

OTHER PUBLICATIONS

Au, C. T. et al., "The oxidative coupling of methane over $BaCO_3/LaOCl$ catalysts", Applied Catalysis A: General, vol. 159 (1997) pp. 133-145.

(Continued)

*Primary Examiner*—Johann Richter
*Assistant Examiner*—Sikarl A. Witherspoon
(74) *Attorney, Agent, or Firm*—Marie F. Zuckerman

(57) ABSTRACT

An oxidative halogenation and optional dehydrogenation process involving contacting a reactant hydrocarbon having three or more carbon atoms, such as propane or propene, or a halogenated derivative thereof, with a source of halogen, and optionally, a source of oxygen in the presence of a rare earth halide or rare earth oxyhalide catalyst, so as to form a halogenated hydrocarbon product, such as allyl chloride, having three or more carbon atoms and having a greater number of halogen substituents as compared with the reactant hydrocarbon, and optionally, an olefinic co-product, such as propene. The less desired of the two products, that is, the halogenated hydrocarbon or the olefin as the case may be, can be recycled to the process to maximize the production of the desired product.

29 Claims, No Drawings

U.S. PATENT DOCUMENTS

| | | | | |
|---|---|---|---|---|
| 4,859,432 A | 8/1989 | David et al. | ............... | 423/21.1 |
| 4,899,000 A | 2/1990 | Stauffer | ...................... | 570/222 |
| 4,942,697 A | 7/1990 | Khaladji et al. | ........... | 51/283 R |
| 4,965,057 A | 10/1990 | David et al. | ................ | 423/263 |
| 5,008,225 A | 4/1991 | Magistro | ...................... | 502/73 |
| 5,013,534 A | 5/1991 | Dissaux et al. | ............. | 423/263 |
| 5,023,070 A | 6/1991 | Le Loarer | ................... | 423/592 |
| 5,061,670 A | 10/1991 | Forquy et al. | ............... | 585/500 |
| 5,072,063 A | 12/1991 | Langensee | .................. | 570/236 |
| 5,087,791 A | 2/1992 | Magistro | ...................... | 585/657 |
| 5,097,083 A | 3/1992 | Stauffer | ...................... | 570/241 |
| 5,099,085 A | 3/1992 | Strasser et al. | ............. | 570/245 |
| 5,113,027 A | 5/1992 | Mainz et al. | ............... | 570/224 |
| 5,114,702 A | 5/1992 | Pederson et al. | ........... | 423/639 |
| 5,137,862 A | 8/1992 | Mackrodt et al. | ........... | 502/303 |
| 5,178,664 A | 1/1993 | Picard | ......................... | 75/300 |
| 5,179,215 A | 1/1993 | Ramachandran et al. | ... | 549/262 |
| 5,210,358 A | 5/1993 | Magistro | ..................... | 585/500 |
| 5,227,549 A | 7/1993 | Correia et al. | ............... | 570/243 |
| 5,232,889 A | 8/1993 | Blanchard et al. | ........... | 502/263 |
| 5,262,547 A | 11/1993 | Ramachandran et al. | ... | 549/262 |
| 5,352,646 A | 10/1994 | Blanchard et al. | ........... | 502/263 |
| 5,397,758 A | 3/1995 | Bouruetaubertot et al. | . | 502/303 |
| 5,453,557 A | 9/1995 | Harley et al. | ................ | 585/641 |
| 5,466,837 A | 11/1995 | Ramachandran et al. | ... | 549/533 |
| 5,492,878 A | 2/1996 | Fujii et al. | ................... | 502/304 |
| 5,496,528 A | 3/1996 | David et al. | ................. | 423/263 |
| 5,510,546 A | 4/1996 | Ito | .............................. | 570/236 |
| 5,580,536 A | 12/1996 | Yao et al. | .................... | 423/263 |
| 5,599,588 A | 2/1997 | Poncelet | ...................... | 427/343 |
| 5,600,042 A | 2/1997 | Chen et al. | .................. | 570/230 |
| 5,607,890 A | 3/1997 | Chen et al. | .................. | 205/202 |
| 5,646,304 A | 7/1997 | Acharya et al. | ............. | 549/259 |
| 5,663,112 A | 9/1997 | Ahn et al. | ................... | 502/304 |
| 5,663,465 A | 9/1997 | Clegg et al. | ................. | 570/224 |
| 5,663,472 A | 9/1997 | Benson et al. | ............... | 585/641 |
| 5,705,728 A | 1/1998 | Viswanathan et al. | ...... | 585/641 |
| 5,728,905 A | 3/1998 | Clegg et al. | ................. | 570/224 |
| 5,762,894 A | 6/1998 | Takatori et al. | ............. | 423/263 |
| 5,763,710 A | 6/1998 | Clegg et al. | ................. | 570/224 |
| 5,773,383 A | 6/1998 | Suciu | .......................... | 502/355 |
| 5,874,380 A | 2/1999 | Chen et al. | .................. | 502/217 |
| 5,877,371 A | 3/1999 | Chen et al. | .................. | 585/467 |
| 5,880,058 A | 3/1999 | Moriya et al. | .............. | 502/302 |
| 5,883,037 A | 3/1999 | Chopin et al. | ............... | 502/308 |
| 5,898,014 A | 4/1999 | Wu et al. | .................... | 502/302 |
| 5,905,177 A | 5/1999 | Seo et al. | .................... | 570/232 |
| 5,919,727 A | 7/1999 | Brezny | ........................ | 502/304 |
| 5,922,639 A | 7/1999 | Alario et al. | ................. | 502/230 |
| 5,925,590 A | 7/1999 | White et al. | ................. | 502/302 |
| 5,935,897 A | 8/1999 | Trubenbach et al. | ... | 502/527.14 |
| 5,935,898 A | 8/1999 | Trubenbach et al. | ... | 502/527.14 |
| 5,945,370 A | 8/1999 | Yokoi et al. | ................. | 502/304 |
| 5,945,173 A | 8/1999 | Nappa et al. | ................. | 570/175 |
| 5,955,638 A | 9/1999 | Schoebrechts et al. | ...... | 570/232 |
| 5,969,195 A | 10/1999 | Stabel et al. | ................ | 568/700 |
| 5,972,827 A | 10/1999 | Petit et al. | ................... | 502/225 |
| 5,972,830 A | 10/1999 | Yoshida et al. | ............. | 502/304 |
| 5,994,260 A | 11/1999 | Bonneau et al. | ............ | 502/304 |
| 6,002,019 A | 12/1999 | Tamhankar et al. | ......... | 549/285 |
| 6,090,743 A | 7/2000 | Chopin et al. | ............... | 502/302 |
| 6,136,048 A | 10/2000 | Birchem et al. | .............. | 44/354 |
| 6,165,931 A | 12/2000 | Rao | ............................ | 502/224 |
| 6,191,329 B1 | 2/2001 | Benje | ......................... | 570/243 |
| 6,194,345 B1 | 2/2001 | Mangnus et al. | ........... | 502/224 |
| 6,228,799 B1 | 5/2001 | Aubert et al. | ................ | 502/304 |
| 6,452,058 B1 | 9/2002 | Schweizer et al. | .......... | 570/223 |
| 6,680,415 B1 | 1/2004 | Gulotty, Jr. et al. | ........ | 570/243 |
| 6,821,924 B2 | 11/2004 | Gulotty, Jr. et al. | | |

FOREIGN PATENT DOCUMENTS

| | | |
|---|---|---|
| EP | 0 162 457 B1 | 7/1989 |
| EP | 0 720 975 A1 | 7/1996 |
| EP | 0 372 183 B1 | 1/1997 |
| EP | 0 667 845 B1 | 1/1998 |
| FR | 1 594 693 | 7/1970 |
| GB | 1 343 724 | 1/1874 |
| GB | 1 039 369 | 8/1966 |
| GB | 1 040 962 | 9/1966 |
| GB | 1 062 171 | 3/1967 |
| GB | 1 141 369 | 1/1969 |
| GB | 1 213 202 | 11/1970 |
| GB | 1 373 296 | 11/1974 |
| GB | 1 475 358 | 6/1977 |
| GB | 1 492 945 | 11/1977 |
| GB | 2 095 242 | 9/1982 |
| GB | 2 101 596 | 1/1993 |
| WO | 01/38271 | 5/2001 |
| WO | 01/38272 | 5/2001 |
| WO | 01/38273 | 5/2001 |
| WO | 01/38274 | 5/2001 |
| WO | 01/38275 | 5/2001 |
| WO | 01/42176 | 6/2001 |
| WO | 02/094749 | 11/2002 |
| WO | 02/094751 A3 | 11/2002 |
| WO | 02/094752 | 11/2002 |

OTHER PUBLICATIONS

Chanaud, P. et al., "Catalytic Membrane Reactor for Oxidative Coupling of Methane. Part 1: Preparation and Characterization of LaOCl Membranes", Catalysis Today, vol. 25 (1995) pp. 225-230.

Chanaud, P. et al., "Study of Lanthanum-based Colloidal Sols Formation", Journal of Materials Science, vol. 29 (1994) pp. 4244-4251.

Conner, Jr., Wm. Curtis et al., "The Oxyhydrochlorination of Methane on Fumed Silica-Based Cu, K, La Catalysts: III Bulk & Surface Analysis", Applied Catalysis, vol. 11 (1984) pp. 59-71.

Conner, Jr., Wm. C. et al., "The Oxyhydrochlorination of Methane on Fumed Silica-Based Cu, K, La Catalysts: II Gas Phase Stoichiometry", Applied Catalysis, vol. 11 (1984) pp. 49-58.

Fells, Ian, "The Kinetics of the Hydrolysis of the Chlorinate Methanes", Fuel Society Journal, vol. 10 (1959) pp. 26-35.

Fortini, E. M. et al., "Stabilization of the Active Phase by Interaction with the Support in $CuCl_2$ Oxychlorination Catalysts", Journal of Catalysis, vol. 99 (1986) pp. 12-18.

Lance, E. T. et al., "Preparation, Phase Equilibria, and Crystal Chemistry of Lanthanum, Praseodymium, and Neodymium Hydroxide Chlorides", Journal of Solid State Chemistry, vol. 17 (1976) pp. 55-60.

Lin, S. et al, "Oxidative Dehydrogenation of Ethane over Lanthanum-Substituted Layered Complex Bismuth Chloride Oxide Catalysts", The Chemical Society of Japan, Chemistry Letters (1997) pp. 901-902.

McDonald, Mark A. et al., "Effects of Pressure on the Oxyhydrochlorination of Methane", Chemical Engineering Science, vol. 49, No. 24A (1994) pp. 4627-4637.

Miyake, Takanori et al., "Screening of Metal Chloride Catalysts for Oxychlorination of Propene", Applied Catalysis A: General, vol. 121, No. 1 (1995) pp. L13-L17.

Noceti, Richard P. et al., "Advances in Methane Oxyhydrochlorination Catalysts", Preprints, American Chemical Society, Washington, DC (1992) pp. 281-283.

Olah, George A. et al., "Selective Monohalogenation of Methane over Supported Acid or Platinum Metal Catalysts and Hydrolysis of Methyl Halides over γ-Alumina-Supported Metal Oxide/Hydroxide Catalysts. A Feasible Path for the Oxidative Conversion of Methane into Methyl Alcohol/Dimethyl Ether", American Chemical Society, vol. 107, No. 24 (1985) pp. 7097-7105.

Patent Abstracts of Japan, vol. 004, No. 190 (Dec. 26, 1980) (Corresponds to JP 55 130923).

Pieters, W.J.M. et al., "The Oxyhydrochlorination of Methane on Fumed Silica—Based $Cu^{+1}$, K, La Catalysts: I. Catalyst Synthesis", Applied Catalysis, vol. 11 (1984) pp. 35-48.

Poznanski, J., "A Study of the Chlorination of Lanthanum and Neodymium Oxides", Materials Science, XVIII (1992) pp. 99-104.

Weckhuysen, Bert M. et al., "Destructive Absorption of Carbon Tetrachloride on Lanthanum and Cerium Oxides", Phys. Chem. Chem. Phys., vol. 1 (1999) pp. 3157-3162.

Weissermel, K. et al., Industrial Organic Chemistry, 2nd Edition, VCH, Weinheim (1993) pp. 168-175.

Derwent Publication, AN 1978-85275A, "Allyl chloride prepn. from propylene, hydrogen chloride and oxygen—using catalyst comprising chloride of samarium, chromium, manganese or praseodymium", Research Disclosure RD-175041, Anonymous.

"Process for Vinyl Chloride Manufacture from Ethane and Ethylene with Secondary Reactive Consumption of Reactor Effluent HCI", filed in the United States Receiving Office on May 14, 2002, U.S. Appl. No. 10/130,105, Applicant: Mark E. Jones et al. (Corresponds to WO 01/38272).

"Production of Vinyl Halide from Single Carbon Feedstocks", filed in the United States Receiving Office on Nov. 18, 2003, U.S. Appl. No. 10/130,105, Applicant: Mark E. Jones et al. (Corresponds to WO 02/09749).

"Process for Vinyl Chloride Manufacture from Ethane and Ethylene with Air Feed and Alternative HCI Processing", filed in the United States Receiving Office on Nov. 11, 2003, U.S. Appl. No. 10/477,502, Applicant: William D. Clarke et al. (Corresponds to WO 02/094752).

"Dehydrogenation of Halogenated Alkanes Using Rare Earth Halide or Oxyhalide Catalyst", filed in the United States Receiving Office on May 14, 2002, U.S. Appl. No. 10/130,106, Applicant: Larry N. Ito et al. (Corresponds to WO 01/38275).

"A Process for the Conversion of Ethylene to Vinyl Chloride, and Novel Catalyst Compositions Useful for Such Process", filed in the United States Receiving Office on May 14, 2002, U.S. Appl. No. 10/130,104, Applicant: Mark E. Jones et al. (Corresponds to WO 01/38273).

"Process for Vinyl Chloride Manufacture From Ethane and Ethylene with Partial HCI Recovery From Reactor Effluent", filed in the United States Receiving Office on May 14, 2002, U.S. Appl. No. 10/130,102, Applicant: John P. Henley et al. (Corresponds to WO 01/42176).

"Process for Vinyl Chloride Manufacture From Ethane and Ethylene with Partial HCI Recovery From Reactor Effluent", filed in the United States Receiving Office on May 14, 2002, U.S. Appl. No. 10/130,103, Applicant: Daniel A. Hickman et al. (Corresponds to WO 01/38274).

OXIDATIVE HALOGENATION AND OPTIONAL DEHYDROGENATION OF C3+HYDROCARBONS

Cross-Reference to Related Applications: This application is a 371 of International Patent Application no. PCT/US 02/13011, filed Apr. 23, 2002, which claims the benefit of U.S. Provisional Patent Application Ser. No. 60/293,123, filed May 23, 2001.

This invention pertains to a process for the oxidative halogenation and optional dehydrogenation of a reactant hydrocarbon having three or more carbon atoms (hereinafter referred to as a "C3+ hydrocarbon"). For the purposes of this discussion, the term "oxidative halogenation and optional dehydrogenation" shall refer to a process wherein a reactant hydrocarbon having three or more carbon atoms, or a halogenated derivative thereof, is contacted with a source of halogen and, optionally, a source of oxygen so as to form a halogenated hydrocarbon product having three or more carbon atoms and having a greater number of halogen substituents as compared with the reactant hydrocarbon, and optionally, an olefinic hydrocarbon product having three or more carbon atoms.

Olefinic C3+ hydrocarbons and halogenated C3+ hydrocarbons, for example, propene, chloropropanes, and chloropropenes, more preferably, propene, dichloropropane, and ally chloride, find utility in a broad spectrum of applications. Propene (or propylene) is an important olefin feedstock for many useful products, such as polypropylene, isopropyl alcohol, and cumene. Dichloropropane is useful in fumigants and solvent mixtures. Allyl chloride is a precursor to allyl alcohol and epichlorohydrin.

While there are several known methods for preparing propene by the dehydrogenation of propane, none are practiced on a commercial scale, because the methods are too energy and capital intensive. Propene is produced mainly as a co-product in two major petrochemical processes: steam cracking, from which the major products are ethylene, propene, butenes and butadiene, and catalytic cracking, from which the major products are naphtha (gasoline), propene, and butenes. Both of these processes provide essentially all of the propene that the market has needed up to this time. As propene demand increases more rapidly than the market for ethylene and/or gasoline, it would be useful to have a route to propene that is not tied to these other products.

The uncatalyzed oxidative halogenation of olefinic hydrocarbons having three or more carbon atoms, such as propene, with chlorine to the corresponding unsaturated halogenated hydrocarbons, such as chloropropenes, referred to as the "hot chlorination route," is described in the following representative art of K. Weissermel and H.-J. Arpe, *"Industrial Organic Chemistry"*, $2^{nd}$ edition, VCH Verlagsgesellschaft mbH, Weinheim, pp. 291–293. The process, while efficient, is disadvantageously conducted at high temperatures.

The reactions of halogens with saturated C3+ hydrocarbons by both-talyzed and catalytic routes have also been reported in the art; see for example, Olah and Molnar *"Hydrocarbon Chemistry,"* John Wiley & Sons, 1995, pp. 415–432, and Wittcoff and Reuben *"Industrial Organic Chemicals,"* John Wiley & Sons, 1996, pp. 338–341. Catalyzed routes are also reported by Weissermel and Arpe, *Ibid*, p. 292. The catalyzed routes are not practiced commercially, because the "hot chlorination" route is more efficient and cost effective. In the catalyzed process, however, the reactant hydrocarbon is contacted under reaction conditions with a source of halogen and, optionally, a source of oxygen in the presence of an oxidative halogenation catalyst. Typically, the catalyst contains a copper compound, an iron compound, or cerium oxide, optionally, with one or more alkali or alkaline earth metal chlorides, and/or optionally, with one or more rare earth compounds, supported on an inert carrier, typically alumina, silica, or an aluminosilicate.

Disadvantageously, the catalyzed processes of the prior art produce an unacceptable quantity of highly halogenated products, including perhalogenated products, which are less desirable than the monohalogenated and dihalogenated products. As a further disadvantage, the prior art processes produce an unacceptable quantity of deep oxidation products ($CO_x$), specifically, carbon monoxide and carbon dioxide. The production of lower value highly halogenated products and undesirable oxidized products irretrievably wastes the hydrocarbon feed and creates product separation and by-product disposal problems. As a further disadvantage, many of the transition metal halides used as catalysts for this type of process exhibit significant vapor pressure at reaction temperatures; that is, these catalysts are volatile. The volatility generally produces a decline in catalyst activity and/or deposition of corrosive materials in downstream parts of the process equipment.

As evidenced from the above, the catalyzed oxidative halogenation of hydrocarbons having three or more carbon atoms is substantially non-selective for the corresponding mono- and di-halogenated hydrocarbon products. Accordingly, an increase in selectivity to mono- and di-halogenated hydrocarbons is needed. Likewise, a reduction in selectivities to higher halogenated products, including perhalogenated products, and oxygenated products is needed. Also, increases in catalyst activity and catalyst lifetime are needed. With these improvements, the oxidative halogenation of C3+ hydrocarbons to halogenated C3+ hydrocarbons, preferably, mono- and di-halogenated C3+ hydrocarbons, such as dichloropropane and allyl chloride, and optionally, to unsaturated hydrocabon products, preferably olefins, should be more attractive.

This invention provides for a novel oxidative halogenation and optional dehydrogenation process of preparing a halogenated C3+ hydrocarbon, and optionally, a C3+ olefinic hydrocarbon. The novel process of this invention comprises contacting a reactant hydrocarbon having three or more carbon atoms (a C3+ hydrocarbon), or a halogenated derivative thereof, with a source of halogen and, optionally, a source of oxygen in the presence of a catalyst under process conditions sufficient to prepare a halogenated hydrocarbon product having three or more carbon atoms (a halogenated C3+ hydrocarbon) and having a greater number of halogen substituents as compared with the reactant hydrocarbon. Optionally, a second product is produced comprising an olefinic hydrocarbon having three or more carbon atoms. In this process, it is preferred to employ the source of oxygen. The catalyst employed in this process comprises a rare earth halide or rare earth oxyhalide compound substantially free of copper and iron, with the proviso that when cerium is present in the catalyst, at least one other rare earth element is also present in the catalyst.

The novel oxidative halogenation and optional dehydrogenation process of this invention advantageously converts a reactant hydrocarbon having three or more carbon atoms, or a halogenated derivative thereof, in the presence of a source of halogen and, preferably, a source of oxygen into a halogenated hydrocarbon product having three or more carbon atoms and having an increased number of halogen substituents as compared with the reactant hydrocarbon. Optionally, a second hydrocarbon product may be concurrently produced comprising a C3+ olefinic hydrocarbon. In a preferred embodiment, the process of this invention can be beneficially employed to oxidatively chlorinate propane in the presence of hydrogen chloride and oxygen to allyl chloride and propylene. As compared with prior art processes, the process of this invention advantageously produces halogenated hydrocarbon product, preferably, mono- and di-halogenated hydrocarbon products and, optionally, olefinic hydrocarbon product in high selectivities with essentially no perhalogenated halocarbon by-products and low levels, if any, of undesirable oxygenates, such as, carbon monoxide and carbon dioxide. The lower selectivity to perhalogenated halocarbons and undesirable oxygenated by-products correlates with a more efficient use of reactant hydrocarbon, a higher productivity of the desired lower halogenated hydrocarbon products and optional olefin, and fewer separation and waste disposal problems. As an additional advantage, the less desired product formed, either olefin or halogenated product as the case may be, may be recycled to the oxidative halogenation process to maximize the production of the more desired product.

In addition to the above advantages, the catalyst employed in the process of this invention does not require a conventional carrier or support, such as alumina or silica. Instead, the catalyst employed in this invention beneficially comprises a rare earth halide or rare earth oxyhalide compound that uniquely functions both as a catalyst support and as a source of a further catalytically active rare earth component Unlike many heterogeneous catalysts of the prior art, the rare earth halide catalyst of this invention is beneficially soluble in water. Accordingly, should process equipment, such as filters, valves, circulating tubes, and small or intricate parts of reactors, become plugged with particles of the rare earth halide catalyst, then a simple water wash can advantageously dissolve the plugged particles and restore the equipment to working order. As a further advantage, the catalysts used in the process of this invention are significantly less volatile, as compared with the prior art catalysts. Accordingly, the rare earth halide and rare earth oxyhalide catalysts employed in the process of this invention possess an acceptable reaction rate and a long lifetime, and further, present essentially no downstream contamination or corrosion problems.

All of the aforementioned properties render the process of this invention uniquely attractive for converting a reactant C3+ hydrocarbon, or a halogenated derivative thereof, into a halogenated C3+ hydrocarbon having a greater number of halogen substituents than in the reactant hydrocarbon, and optionally, into a co-product C3+ olefinic hydrocarbon. In preferred embodiments of this invention, mono- and/or di-halogenated hydrocarbon products are selectively produced along with the olefin. As a most preferred advantage, the process of this invention can oxidatively dehydrogenate and halogenate propane selectivity to propene and monohalogenated propene, preferably, allyl chloride or allyl bromide.

In the novel oxidative halogenation and optional dehydrogenation process of this invention, a halogenated hydrocarbon product having three or more carbon atoms, preferably a mono- and/or di-halogenated hydrocarbon product having three or more carbon atoms, and an optional olefinic co-product are selectively produced with essentially no formation of perhalogenated chlorocarbon product and with advantageously low levels of undesirable oxygenated by-products, such as, $CO_x$ oxygenates (CO and $CO_2$). The novel process of this invention comprises contacting a hydrocarbon having three or more carbon atoms (a C3+ hydrocarbon), or a halogenated derivative thereof, with a source of halogen and, optionally, a source of oxygen in the presence of a catalyst under process conditions sufficient to prepare a halogenated hydrocarbon product having three or more carbon atoms (a halogenated C3+ hydrocarbon) and having a greater number of halogen substituents as compared with the reactant hydrocarbon. Optionally, a co-product comprising an olefin having three or more carbon atoms is formed in the process. In a preferred embodiment of the invention, the source of oxygen is employed. The unique catalyst employed in the oxidative halogenation and optional dehydrogenation process of this invention comprises a rare earth halide or rare earth oxyhalide compound that is substantially free of copper and iron, with the further proviso that when cerium is present in the catalyst, at least one other rare earth element is also present in the catalyst.

The term "oxidative halogenation and optional dehydrogenation" shall in some occurrences hereinafter be simply referred to "oxidative halogenation." This shortened term is used for convenience only and shall not limit the process in any fashion. The process of this invention shall include both halogenation reactions wherein halogenated products are formed as well as dehydrogenation reactions wherein less saturated hydrocarbon products (for example, olefins) are formed, as compared with the reactant hydrocarbons (for example, alkanes).

In a preferred embodiment of this invention, the process produces as a co-product a C3+ olefin, preferably, propylene. The co-product olefin can be advantageously recycled to the oxidative halogenation process for further processing to halogenated hydrocarbons, preferably, allyl chloride.

In another preferred embodiment of this invention, the halogenated hydrocarbon product, such as allyl chloride, can be recycled to the oxidative halogenation process for further processing to olefinic products, such as propylene.

In a more preferred embodiment of this invention, the process comprises contacting propane with a source of halogen and, optionally, a source of oxygen in the presence of a catalyst under process conditions sufficient to prepare allyl halide and propylene, the catalyst comprising a rare earth halide or rare earth oxyhalide that is substantially free of copper and iron, with the further proviso that when cerium is present in the catalyst, at least one other rare earth element is also present in the catalyst. In a most preferred embodiment, the source of halogen is hydrogen chloride; the halogenated C3+ hydrocarbon produced is allyl chloride; and the co-product olefin produced is propylene.

With respect to the catalyst, in a preferred embodiment, the rare earth halide or rare earth oxyhalide catalyst is "porous," which, for the purposes of this invention, means that the catalyst has a surface area of least 5 $m^2/g$, as determined by the BET (Brunauer-Emmet-Teller) method of measuring surface area, described by S. Brunauer, P. H. Emmett, and E. Teller, *Journal of the American Chemical Society*, 60, 309 (1938). In another more preferred embodiment of this invention, the rare earth halide is lanthanum chloride, and the rare earth oxyhalide is lanthanum oxychloride.

The reactant hydrocarbon used in the oxidative halogenation process of this invention comprises a hydrocarbon having three or more carbon atoms or a halogenated hydrocarbon having three or more carbon atoms, either being capable of acquiring more halogen substituents in accordance with the process described herein. The halogen substituent of the halogenated reactant hydrocarbon is preferably selected from chlorine, bromine, iodine, and mixtures thereof, more preferably, chlorine and bromine. One, two, or three halogen substituents may be present on the halogenated hydrocarbon; but for the purposes of this invention the reactant halogenated hydrocarbon is not a perhalogenated compound, as in hexachloropropane. Different halogen substituents may be suitably present in the halogenated hydrocarbon reactant, as illustrated by bromochloropropane and the like. Suitable examples of reactant hydrocarbons and reactant halogenated hydrocarbons include, without limitation, alkanes and alkenes, and halogenated derivatives thereof, including propane, butane, pentane, chloropropane, chlorobutane, dichloropropane, dichlorobutane, bromopropane, bromobutane, dibromopropane, dibromobutane, bromochloropropane, and the like, including higher homologues thereof. Likewise, cyclic aliphatic hydrocarbons, such as cyclohexane, and aromatic hydrocarbons, such as benzene, ethylbenzene, and cumene, including alkyl and halo substituted cyclic aliphatics and aromatics, may be employed. Preferably, the reactant hydrocarbon or reactant halogenated hydrocarbon is a $C_{3-20}$ hydrocarbon, more preferably, a $C_{3-10}$ hydrocarbon. The most preferred reactant hydrocarbon is selected from propane and propene. The reactant hydrocarbon may be provided to the oxidative halogenation process as a pure feed stream, or diluted with an inert diluent as described hereinafter, or as a mixture of reactant hydrocarbons, optionally, further in combination with an inert diluent.

The source of halogen, which is employed in the process of this invention, may be any inorganic or organic halogen-containing compound that is capable of transferring its halogen atom(s) to the reactant hydrocarbon. Suitable non-limiting examples of the source of halogen include chlorine, bromine, iodine, hydrogen chloride, hydrogen bromide, hydrogen iodide, and halogenated hydrocarbons having one or more labile halogen substituents (that is, transferable halogen substituents). Examples of the latter include perhalocarbons, such as carbon tetrachloride and carbon tetrabromide, as well as highly halogenated hydrocarbons having, for example, three or more halogen atoms. Non-limiting examples of highly halogenated hydrocarbons having three or more halogen substituents, at least one substituent of which is labile, include chloroform and tribromomethane. Preferably, the source of halogen is a source of chlorine or a source of bromine, more preferably, hydrogen chloride or hydrogen bromide, most preferably, hydrogen chloride.

The source of halogen may be provided to the process in any amount that is effective in producing the desired halogenated hydrocarbon product. Typically, the amount of halogen source will vary depending upon the specific process stoichiometry, the reactor design, and safety considerations. It is possible, for example, to use a stoichiometric amount of halogen source with respect to the reactant hydrocarbon or with respect to oxygen, if oxygen is present. Alternatively, the source of halogen may be used in an amount that is greater or less than the stoichiometric amount, if desired. In one embodiment illustrative of the invention, propane can be oxidatively chlorinated with chlorine to form chloropropane and hydrogen chloride, the stoichiometric reaction of which is shown in Equation (I) hereinafter:

$$CH_3CH_2CH_3 + Cl_2 \rightarrow CH_3CHClCH_3 + HCl \qquad (I)$$

The aforementioned process, which does not employ oxygen, would usually be conducted at a stoichiometric molar ratio of chlorine to propane or at a higher than stoichiometric molar ratio of chlorine to propane (molar ratio $\geq 1$ $Cl_2$:1 $CH_3CH_2CH_3$), and preferably, would be conducted in an excess of chlorine to ensure complete conversion of propane. In this embodiment of the invention, the molar ratio of source of halogen to reactant hydrocarbon is generally greater than 1/1, preferably, greater than 2/1, and more preferably, greater than 4/1. Generally, in this embodiment of the invention the molar ratio of source of halogen to reactant hydrocarbon is less than 20/1, preferably, less than 15/1, and more preferably, less than 10/1.

In another embodiment illustrative of the invention, propane can be oxidatively chlorinated and dehydrogenated with hydrogen chloride in the presence of oxygen to produce allyl chloride, propylene, and water, the stoichiometric reaction of which is shown hereinafter in Equation (II):

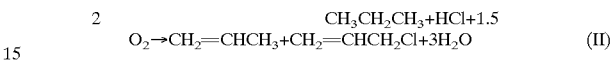

$$2 O_2 \rightarrow CH_2=CHCH_3 + CH_2=CHCH_2Cl + 3H_2O \qquad (II)$$

(with $CH_3CH_2CH_3 + HCl + 1.5$)

This embodiment of the process, which employs oxygen, is usually conducted "fuel-rich," due to safety considerations. The term "fuel-rich" means that oxygen is the limiting reagent and a molar excess of reactant hydrocarbon is used relative to oxygen. Typically, for example, the molar ratio of hydrocarbon to oxygen is chosen for operation outside the fuel-rich flammability limit of the mixture, although this is not absolutely required. In addition, a stoichiometric molar ratio of hydrogen halide to oxygen (for example, 1 HCl:1.5 $O_2$) is typically employed to ensure complete reaction of both the source of halogen and oxygen.

A source of oxygen is not required for the process of this invention; however, use of a source of oxygen is preferred, particularly when the source of halogen contains hydrogen atoms. The source of oxygen can be any oxygen-containing gas, such as, commercially pure molecular oxygen, air, oxygen-enriched air, or a mixture of oxygen with a diluent gas that does not interfere with the oxidative halogenation process, such as, nitrogen, argon, helium, carbon monoxide, carbon dioxide, methane, and mixtures thereof. As noted above, when oxygen is employed, the feed to the oxidative halogenation reactor is generally fuel-rich. Typically, the molar ratio of reactant hydrocarbon to oxygen is greater than 2/1, preferably, greater than 4/1, and more preferably, greater than 5/1. Typically, the molar ratio of reactant hydrocarbon to oxygen is less than 20/1, preferably, less than 15/1, and more preferably, less than 10/1.

Based on the description hereinabove, one skilled in the art will know how to determine the molar quantities of reactant C3+ hydrocarbon, source of halogen, and source of oxygen suitable for reactant combinations different from those illustrated herein.

Optionally, if desired, the feed, comprising reactant hydrocarbon, source of halogen, and optional source of oxygen, can be diluted with a diluent or carrier gas, which may be any essentially non-reactive gas that does not substantially interfere with the oxidative halogenation process. The diluent may assist in removing products and heat from the reactor and in reducing the number of undesirable side-reactions. Non-limiting examples of suitable diluents include nitrogen, argon, helium, carbon monoxide, carbon dioxide, methane, and mixtures thereof. The quantity of diluent employed is typically greater than 10 mole percent, and preferably, greater than 20 mole percent, based on the total moles of feed to the reactor, that is, total moles of reactant hydrocarbon, source of halogen, source of oxygen, and diluent. The quantity of diluent employed is typically less than 90 mole percent, and preferably, less than 70 mole percent, based on the total moles of feed to the reactor.

The catalyst employed in the oxidative halogenation process of this invention comprises, in one aspect, a rare earth halide compound. The rare earths are a group of 17 elements consisting of scandium (atomic number 21), yttrium (atomic number 39) and the lanthanides (atomic numbers 57–71) [James B. Hedrick, U.S. Geological Survey—Minerals Information—1997, "Rare-Earth Metals"]. Preferably, herein, the term is taken to mean an element selected from lanthanum, cerium, neodymium, praseodymium, dysprosium, samarium, yttrium, gadolinium, erbium, ytterbium, holmium, terbium, europium, thulium, lutetium, and mixtures thereof Preferred rare earth elements for use in the aforementioned oxidative halogenation process are those that are typically considered as being single valency metals. The catalytic performance of rare earth halides using multi-valency metals appears to be less desirable than rare earth halides using single valency metals. The rare earth element for this invention is preferably selected from lanthanum, praeseodyrnium, neodymium, and mixtures thereof. Most preferably, the rare earth element used in the catalyst is lanthanum or a mixture of lanthanum with other rare earth elements.

Preferably, the rare earth halide is represented by the formula $MX_3$ wherein M is at least one rare earth element selected from the group consisting of lanthanum, cerium, neodymium, praseodymium, dysprosium, samarium, yttrium, gadolinium, erbium, ytterbium, holmium, terbium, europium, thulium, lutetium, and mixtures thereof; and wherein each X is independently selected from chloride, bromide, and iodide. More preferably, X is chloride, and the more preferred rare earth halide is represented by the formula $MCl_3$, wherein M is defined hereinbefore. Most preferably, X is chloride and M is lanthanum or a mixture of lanthanum with other rare earth elements.

In a preferred embodiment, the rare earth halide is porous, meaning that typically the rare earth halide has a BET surface area of greater than 5 $m^2/g$. Preferably, the BET surface area is greater than about 10 $m^2/g$, more preferably, greater than about 15 $m^2/g$, even more preferably, greater than about 20 $m^2/g$, and most preferably, greater than about 30 $m^2/g$. For these above measurements, a nitrogen adsorption isotherm was measured at 77K and the surface area was calculated from the isotherm data utilizing the BET method, as referenced earlier herein.

In another aspect, the catalyst employed in this invention comprises a rare earth oxyhalide, the rare earths being the seventeen elements identified hereinabove. Preferably, the rare earth oxyhalide is represented by the formula MOX, wherein M is at least one rare earth element selected from the group consisting of lanthanum, cerium, neodymium, praseodymium, dysprosium, samarium, yttrium, gadolinium, erbium, ytterbium, holmium, terbium, europium, thulium, lutetium, and mixtures thereof; and wherein each X is independently selected from the group consisting of chloride, bromide, and iodide. More preferably, the rare earth halide is a rare earth oxychloride, represented by the formula MOCl, wherein M is defined hereinbefore. Most preferably, X is chloride, and M is lanthanum or a mixture of lanthanum with other rare earth elements.

In a preferred embodiment, the rare earth oxyhalide is also porous, which generally implies a BET surface area of greater than about 12 $m^2/g$. Preferably, the rare earth oxyhalide has a BET surface area of greater than about 15 $m^2/g$, more preferably, greater than about 20 $m^2/g$, and most preferably, greater than about 30 $m^2/g$. Generally, the BET surface area of the rare earth oxyhalide is less than about 200 $m^2/g$. In addition, it is noted that the MOCl phases possess characteristic powder X-Ray Diffraction (XRD) patterns that are distinct from the $MCl_3$ phases.

In general, the presence in the catalyst of metals that are capable of oxidation-reduction (redox) is undesirable. Redox metals typically include transition metals that have more than one stable oxidation state, such as iron, copper, and manganese. The rare earth halide or oxyhalide catalyst of this invention is specifically required to be substantially free of copper and iron. The term "substantially free" means that the atom ratio of rare earth element to redox metal, preferably iron or copper, is greater than about 1/1, preferably greater than about 10/1, more preferably greater than about 15/1, and most preferably greater than about 50/1. In addition, cerium, a lanthanide rare earth element, is known to be an oxidation-reduction catalyst having the ability to access both the $3^+$ and $4^+$ oxidation states. For this reason, if the rare earth metal is cerium, the catalyst of this invention further comprises at least one more rare earth metal other than cerium. Preferably, if one of the rare earth metals is cerium, the cerium is provided in a molar ratio that is less than the total amount of other rare earth metals present in the catalyst. More preferably, however, substantially no cerium is present in the catalyst. By "substantially no cerium" it is meant that any cerium present is in an amount less than about 10 atom percent, preferably, less than about 5 atom percent, and even more preferably, less than about 1 atom percent of the total rare earth components.

In an alternative embodiment of this invention, the rare earth halide or rare earth oxyhalide catalyst, described hereinbefore, may be bound to, extruded with, or deposited onto a conventional catalyst support, such as alumina, silica, silica-alumina, porous aluminosilicate (zeolite), silica-magnesia, bauxite, magnesia, silicon carbide, titanium oxide, zirconium oxide, zirconium silicate, or any combination thereof. In this embodiment, the conventional support is used in a quantity greater than about 1 weight percent, but less than about 90 weight percent, preferably, less than about 70 weight percent, more preferably, less than about 50 weight percent, based on the total weight of the catalyst and catalyst support.

It may also be advantageous to include other elements within the catalyst. For example, preferable elemental additives include alkali and alkaline earths, boron, phosphorous, sulfur, germanium, titanium, zirconium, hafnium, and combinations thereof. These elements can be present to alter the catalytic performance of the composition or to improve the mechanical properties (for example attrition-resistance) of the material. In a preferred embodiment, the elemental additive is calcium. In another preferred embodiment, the elemental additive is not aluminum or silicon. The total concentration of elemental additives in the catalyst is typically greater than about 0.01 weight percent and typically less than about 20 weight percent, based on the total weight of the catalyst.

The rare earth halide and rare earth oxyhalide compounds may be obtained commercially or prepared by methods published in the art. A method currently felt to be preferable for forming the porous rare earth oxyhalide (MOX) comprises the following steps: (a) preparing a solution of a halide salt of the rare earth element or elements in a solvent comprising either water, an alcohol, or mixtures thereof; (b) adding a base to cause the formation of a precipitate; and (c) collecting and calcining the precipitate in order to form the MOX. Preferably, the halide salt is a rare earth chloride salt, for example, any commercially available rare earth chloride. Typically, the base is a nitrogen-containing base selected from ammonium hydroxide, alkyl amines, aryl amines, arylalkyl amines, alkyl ammonium hydroxides, aryl ammonium hydroxides, arylalkyl ammonium hydroxides, and mixtures thereof. The nitrogen-containing base may also be provided as a mixture of a nitrogen-containing base with other bases that do not contain nitrogen. Preferably, the nitrogen-containing base is ammonium hydroxide or tetra (alkyl)ammonium hydroxide, more preferably, tetra($C_{1-20}$ alkyl)ammonium hydroxide. Porous rare earth oxyhalides may also be produced by appropriate use of alkali or alkaline earth hydroxides, particularly, with the buffering of a nitrogen-containing base, although caution should be exercised to avoid producing substantially the rare earth hydroxide or oxide. The solvent in Step (a) is preferably water. Generally, the precipitation is conducted at a temperature greater than about 0° C. Generally, the precipitation is conducted at a temperature less than about 200° C., preferably, less than about 100° C. The precipitation is conducted generally at about-ambient atmospheric pressure, although higher pressures may be used, as necessary, to maintain liquid phase at the precipitation temperature employed. The calcination is typically conducted at a temperature greater than about 200° C., preferably, greater than about 300° C., and less than about 800° C., preferably, less than about 600° C. Production of mixed carboxylic acid and rare earth halide salts also can yield rare earth oxyhalides upon appropriate decomposition.

A method currently felt to be preferable for forming the porous rare earth halide ($MX_3$) catalyst comprises the following steps: (a) preparing a solution of a halide salt of the rare earth element or elements in a solvent comprising either water, an alcohol, or mixtures thereof; (b) adding a base to cause the formation of a precipitate; (c) collecting and calcining the precipitate; and (d) contacting the calcined precipitate with a halogen source. Preferably, the rare earth halide is a rare earth chloride salt, such as any commercially available rare earth chloride. The solvent and base may be any of those mentioned hereinbefore in connection with the formation of MOX. Preferably, the solvent is water, and the base is a nitrogen-containing base. The precipitation is generally conducted at a temperature greater than about 0° C. and less than about 200° C., preferably less than about 100° C., at about ambient atmospheric pressure or a higher pressure so as to maintain liquid phase. The calcination is typically conducted at a temperature greater than about 200° C., preferably, greater than about 300° C., but less than about 800° C., and preferably, less than about 600° C. Preferably, the halogen source is a hydrogen halide, such as hydrogen chloride, hydrogen bromide, or hydrogen iodide. More preferably, the halogen source is hydrogen chloride. The contacting with the halogen source is typically conducted at a temperature greater than about 100° C. and less than about 500° C. Typical pressures for the contacting with the source of halogen range from about ambient atmospheric pressure to pressures less than about 150 psia (1,034 kPa).

As noted hereinabove, the rare earth oxyhalide (MOX) compound can be converted into the rare earth halide ($MX_3$) compound by treating the oxyhalide with a source of halogen. Since the oxidative halogenation process of this invention requires a source of halogen, it is possible to contact the rare earth oxyhalide with a source of halogen, such as chlorine, in the oxidative halogenation reactor to form the $MX_3$ catalyst in situ.

The oxidative halogenation, and optional dehydrogenation, process of this invention can be conducted in a reactor of any conventional design suitable for gas or liquid phase processes, including batch, fixed bed, fluidized bed, transport bed, continuous and intermittent flow reactors, and catalytic distillation reactors. The process conditions (for example, molar ratio of feed components, temperature, pressure, weight hourly space velocity), can be varied widely, provided that the desired halogenated C3+ hydrocarbon product, preferably mono- or di-halogenated C3+ hydrocarbon product, and optionally, the desired olefinic product, are obtained. Typically, the process temperature is greater than about 100° C., preferably, greater than about 150° C., and more preferably, greater than about 200° C. Typically, the process temperature is less than about 600° C., preferably, less than about 500° C., and more preferably, less than about 450° C. Ordinarily, the process can be conducted at atmospheric pressure; but operation at higher or lower pressures is possible, as desired. Preferably, the pressure is equal to or greater than about 14 psia (97 kPa), but less than about 150 psia (1,034 kPa). Typically, the total weight hourly space velocity (WHSV) of the feed (reactant hydrocarbon, source of halogen, optional source of oxygen, and optional diluent) is greater than about 0.1 gram total feed per g catalyst per hour ($h^{-1}$), and preferably, greater than about 1 $h^{-1}$. Typically, the total weight hourly space velocity of the feed is less than about 1,000 $h^{-1}$, and preferably, less than about 100 $h^{-1}$.

If the oxidative halogenation and optional dehydrogenation process is conducted as described hereinabove, then a halogenated hydrocarbon product is formed that has three or more carbon atoms and a greater number of halogen substituents as compared with the reactant hydrocarbon. Halogenated hydrocarbon products beneficially produced by the process of this invention include halogenated alkanes and halogenated alkenes, including, without limitation, chloropropane, allyl chloride, dichloropropane, bromopropane, dibromopropane, allyl bromide, trichloropropane, tribromopropane, and bromochloropropane. Preferably, the halogenated C3+ hydrocarbon product has $C_{3-20}$ carbon atoms, more preferably, $C_{3-10}$ carbon atoms. In another preferred embodiment, the halogenated C3+ hydrocarbon product is a mono- or di-halogenated C3+ product. Most preferably, the halogenated hydrocarbon product is dichloropropane or allyl chloride. In another preferred aspect of this invention, the halogenated alkene product that is formed is selectively halogenated at a terminal carbon position.

In addition to the halogenated C3+ hydrocarbon product, the process of this invention may optionally produce one or more olefins having three or more carbon atoms, non-limiting examples of which include propene, butenes, and higher homologues thereof. Dienes, as well as monoolefins, may be produced. Preferably, the C3+ olefinic product has $C_{3-20}$ carbon atoms, more preferably, $C_{3-10}$ carbon atoms. More preferably, the C3+ olefinic product is propylene.

Typically, in the process of this invention, the number of carbon atoms in the reactant hydrocarbon is essentially conserved in the halogenated hydrocarbon product and the olefinic product. As the carbon chain in the reactant hydrocarbon is lengthened, however, then the possibility increases that some cracking may occur leading to halogenated hydrocarbon products and olefins of shorter chain length, as compared with the reactant hydrocarbon.

In another aspect of this invention, any olefin in the effluent stream, such as propene, may be separated from the halogenated hydrocarbon products and recycled to the oxidative halogenation process for further processing to form halogenated C3+ hydrocarbons, such as, allyl chloride. Likewise, any halogenated product, such as allyl chloride, in the effluent stream may be separated from the olefin products and recycled to the oxidative halogenation process for further processing to form olefinic product, such as propene. The product to be recycled shall depend upon the desired end-product that is to be maximized.

For the purposes of the description herein, "conversion" shall be defined as the mole percentage of reagent that is converted in the oxidative halogenation process of this invention into product(s). Reference may be made to "conversion of reactant C3+ hydrocarbon," or "conversion of source of halogen," or "oxygen conversion." Conversions will vary depending upon the specific reactant, specific catalyst, and specific process conditions under consideration. Typically, for the process of this invention, the conversion of reactant hydrocarbon is greater than about 5 mole percent, preferably, greater than about 15 mole percent, and more preferably, greater than about 30 mole percent. Typically, for the process of this invention, the conversion of the source of halogen is greater than about 10 mole percent, preferably, greater than about 25 mole percent, and more preferably, greater than about 35 mole percent. Typically, the oxygen conversion is greater than about 10 mole percent, preferably, greater than about 20 mole percent, and more preferably, greater than about 40 mole percent.

For the purposes of this invention, "selectivity" shall be defined as the mole percentage of converted reactant hydrocarbon that is converted into a specific product, such as a halogenated hydrocarbon product, olefinic product, or oxygenated by-product, such as CO or $CO_2$. In the oxidative halogenation process of this invention, the selectivity to halogenated hydrocarbon product, preferably, dichloropropane or allyl chloride, is typically greater than about 15 mole percent, preferably, greater than about 25 mole percent, and more preferably, greater than about 30 mole percent. Likewise, the selectivity to olefin is typically greater than about 15 mole percent, preferably, greater than about 25 mole percent, and more preferably, greater than about 35 mole percent. Advantageously, the oxidative halogenation process of this invention produces essentially no perhalogenated products, such as, hexachloropropane, which have lower commercial value. As a further advantage, in preferred embodiments of this invention, low levels of oxygenated by-products, such as $CO_x$ oxygenates (CO and $CO_2$) are produced. Typically, the total selectivity to carbon monoxide and carbon dioxide is less than about 25 mole percent, preferably, less than about 20 mole percent, and more preferably, less than about 15 mole percent.

The following example is provided as an illustration of the process of this invention; but the example should not be construed as limiting the invention in any manner. In light of the disclosure herein, those of skill in the art will recognize alternative embodiments of the invention that fall within the scope of the claims.

EXAMPLE 1

A catalyst composition comprising a porous lanthanum oxychloride was prepared as follows. Lanthanum chloride ($LaCl_3 7H_2O$, 15 g) was dissolved in deionized water (100 ml) in a round-bottom flask. Ammonium hydroxide (6 M, 20 ml) was added to the lanthanum chloride solution with stirring. The mixture was centrifuged, and the excess liquid was decanted to yield a gel. In a separate container, calcium lactate (0.247 g, 0.0008 moles) was dissolved to form a saturated solution in deionized water. The calcium lactate solution was added with stirring to the lanthanum-containing gel. The gel was dried at 120° C. overnight. A dried solid was recovered, which was calcined under air in an open container at 550° C. for 4 hours to yield a porous lanthanum oxychloride catalyst (6.84 g). X-ray diffraction of the solid indicated the presence of a quasi-crystalline form of lanthanum oxychloride. The surface area of the catalyst was 47 $m^2/g$, as measured by the BET method.

The catalyst prepared hereinabove was crushed to 20×40 US mesh (0.85×0.43 mm) and evaluated in the oxidative chlorination and dehydro-genation of propane as follows. A tubular, nickel alloy reactor, having a ratio of length to diameter of 28.6/1 {6 inches (15.24 cm)×0.210 inches (0.533 cm)} was loaded with catalyst (2.02 g). The reactor was fed a mixture of propane, hydrogen chloride, and oxygen in the ratios shown in Table 1. The operating temperature was 400° C., and the operating pressure was atmospheric. The exit gases were analyzed by gas phase chromatography. Results are set forth in Table 1.

TABLE 1

Oxychlorination of Propane Over Lanthanum Catalyst to Allyl Chloride and Propene[1]

| Mole Ratio Propane:HCl: $O_2$:He | WHSV $h^{-1}$ | Conv Propane | Conv HCl | Conv $O_2$ | Sel Propene | Sel[2] Allyl Cl | Sel[2] 1-ClP | Sel CO | Sel $CO_2$ |
|---|---|---|---|---|---|---|---|---|---|
| 1:1:1:7 | 0.1 | 51 | 38 | 48 | 40 | 35 | 10 | 5 | 8 |

[1]Process Conditions: 400° C., atmospheric pressure; conversions and selectivities given as mole percentages.
[2]Allyl Cl = allyl chloride; 1-ClP = 1-chloropropene.

From Table 1 it is seen that the lanthanum oxychloride catalyst is capable of catalyzing the oxidative chlorination and dehydrogenation of propane predominantly to allyl chloride and propene. The catalyst produces lesser amounts of deep oxidation products, such as carbon monoxide and carbon dioxide.

The experimental results presented in Table 1 illustrate the invention under the above-disclosed process and analytical conditions. One skilled in the art will recognize that other results may be obtained depending upon the specific process and analytical conditions employed.

What is claimed is:

1. A process of oxidative halogenation and optional dehydrogenation comprising contacting a reactant alkane having three or more carbon atoms, or a halogenated derivative thereof, with a source of halogen and, optionally, a source of oxygen in the presence of a catalyst under process conditions sufficient to prepare a halogenated hydrocarbon having three or more carbon atoms and having a greater number of halogen substituents as compared with the reactant alkane and sufficient to prepare an olefin having three or more carbon atoms, the catalyst comprising a rare earth halide or rare earth oxyhalide substantially free of iron and copper such that the atom ratio of the rare earth element to iron or copper is greater than about 50/1, with the proviso that when cerium is present in the catalyst, then at least one other rare earth element is also present in the catalyst.

2. The process of claim 1 wherein the reactant alkane is selected from $C_{3-20}$ alkanes.

3. The process of claim 1 wherein the reactant alkane is propane.

4. The process of claim 1 wherein the source of halogen is selected from the group consisting of elemental halogens, hydrogen halides, and halogenated hydrocarbons having one or more labile halogen substituents.

5. The process of claim 4 wherein the source of halogen is elemental chlorine, elemental bromine, or hydrogen chloride.

6. The process of claim 1 wherein the process is conducted at a molar ratio of source of halogen to reactant alkane of greater than 1/1 to less than 20/1.

7. The process of claim 1 wherein the process further comprises oxygen.

8. The process of claim 7 wherein the source of halogen is provided essentially in a stoichiometric amount with respect to the source of oxygen.

9. The process of claim 7 wherein the source of oxygen is selected from the group consisting of molecular oxygen, air, or oxygen-enriched air.

10. The process of claim 7 wherein the process is conducted at a molar ratio of reactant alkane to source of oxygen of greater than 2/1 and less than 20/1.

11. The process of claim 1 wherein the process further comprises a diluent selected from the group consisting of nitrogen, helium, argon, carbon monoxide, carbon dioxide, methane, and mixtures thereof.

12. The process of claim 11 wherein the diluent is used in an amount that is greater than 10 mole percent and less than 90 mole percent, based on the total moles of reactant alkane and diluent.

13. The process of claim 1 wherein the rare earth halide has a BET surface area greater than 5 $m^2/g$.

14. The process of claim 1 wherein the rare earth halide is represented by the formula $MX_3$, wherein M is at least one rare earth element selected from the group consisting of lanthanum, cerium, neodymium, praseodymium, dysprosium, samarium, yttrium, gadolinium, erbium, ytterbium, holmium, terbium, europium, thulium, lutetium, and mixtures thereof; and wherein X is chloride, bromide, or iodide.

15. The process of claim 14 wherein X is chloride, and M is lanthanum or a mixture of lanthanum with other rare earth elements.

16. The process of claim 1 wherein the rare earth oxyhalide has a BET surface area greater than about 12 $m^2/g$.

17. The process of claim 1 wherein the rare earth oxyhalide is represented by the formula MOX, wherein M is at least one rare earth selected from the group consisting of lanthanum, cerium, neodymium, praseodymium, dysprosium, samarium, yttrium, gadolinium, erbium, ytterbium, holmium, terbium, europium, thulium, lutetium, and mixtures thereof; and wherein X is chloride, bromide, or iodide.

18. The process of claim 17 wherein X is chloride, and M is lanthanum or a mixture of lanthanum with other rare earth elements.

19. The process of claim 1 wherein the catalyst is bonded to or extruded with a support.

20. The process of claim 1 wherein the process is conducted at a temperature greater than about 100° C. and less than about 600° C.

21. The process of claim 1 wherein the process is conducted at a pressure equal to or greater than about 14 psia (97 kPa) and less than about 150 psia (1,034 kPa).

22. The process of claim 1 wherein the process is conducted at a weight hourly space velocity of total feed, comprising the reactant alkane, the source of halogen, the optional source of oxygen, and an optional diluent, of greater than about 0.1 $h^{-1}$ and less than about 1,000 $h^{-1}$.

23. The process of claim 1 wherein the halogenated hydrocarbon product is recycled to the process for conversion into olefinic product.

24. The process of claim 1 wherein the olefin is recycled to the process for conversion into halogenated hydrocarbon product.

25. A process of preparing allyl chloride and propylene comprising contacting propane with a source of chlorine and a source of oxygen in the presence of a catalyst at a temperature greater than about 150° C. and less than about 500° C. such that allyl chloride and co-product propylene are formed, the catalyst comprising a rare earth halide or rare earth oxyhalide compound substantially free of iron and copper such that the atom ratio of rare earth element to iron or copper is greater than about 50/1, with the proviso that when cerium is present in the catalyst, then at least one rare earth element is also present in the catalyst.

26. The process of claim 25 wherein the catalyst is a rare earth chloride or rare earth oxychloride.

27. The process of claim 25 wherein the rare earth is lanthanum.

28. The process of claim 25 wherein the co-product propylene is recycled to the process to maximize the production of allyl chloride.

29. The process of claim 25 wherein allyl chloride product is recycled to the reactor to maximize the production of propylene.

* * * * *